(12) United States Patent
Jonelagadda

(10) Patent No.: US 12,396,869 B2
(45) Date of Patent: *Aug. 26, 2025

(54) SYSTEMS AND METHODS FOR USING IMAGE ANALYSIS TO GUIDE A SURGICAL PROCEDURE

(71) Applicant: Kaliber Labs Inc., San Francisco, CA (US)

(72) Inventor: Chandra Jonelagadda, San Francisco, CA (US)

(73) Assignee: Kaliber Labs Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,440

(22) Filed: Apr. 16, 2024

(65) Prior Publication Data
US 2024/0341980 A1 Oct. 17, 2024

Related U.S. Application Data

(63) Continuation of application No. 18/555,252, filed as application No. PCT/US2022/024503 on Apr. 12, 2022, now Pat. No. 12,004,966.
(Continued)

(51) Int. Cl.
*G06T 7/62* (2017.01)
*A61B 1/00* (2006.01)
(Continued)

(52) U.S. Cl.
CPC ...... *A61F 2/4612* (2013.01); *A61B 1/000096* (2022.02); *A61B 1/317* (2013.01);
(Continued)

(58) Field of Classification Search
CPC .. A61F 2/4612; A61F 2002/4633; G06T 7/62; G06T 2207/10016;
(Continued)

(56) References Cited

U.S. PATENT DOCUMENTS 4,600,005 A 7/1986 Hendel
5,215,095 A 6/1993 Macvicar et al.
(Continued)

FOREIGN PATENT DOCUMENTS

EP 2194836 B1 11/2015
JP 2002065585 A 3/2002
(Continued)

OTHER PUBLICATIONS

Antico et al.; Deep learning-based femoral cartilage automatic segmentation in ultrasound imaging for guidance in robotic knee arthroscopy; Ultrasound in medicine & biology; 46(2); pp. 422-435; Nov. 22, 2019.
(Continued)

*Primary Examiner* — Jonathan S Lee
(74) *Attorney, Agent, or Firm* — Shay Glenn LLP

(57) ABSTRACT

Embodiments provide systems and methods to guide a surgery by providing dimensional/shape information. One example comprises receiving imaging data (ID) contained in a video stream captured by an imaging device at a treatment site (TS) and processing the ID. The ID is analyzed to determine ID that depicts a set of anchor structures (AS) in the TS, determine an orientation attribute of each AS of the set with respect to a reference; and determine a respective scale factor (SF) for portions of ID that depict each AS of the set, the respective SF of each portion of the ID reflecting a size distortion of that portion of the ID with respect to a reference scale. Geometric information is determined for at least a portion of the TS where the set of ASs are located and is used to determine shape and dimensions of the graft.

18 Claims, 5 Drawing Sheets

Related U.S. Application Data

(60) Provisional application No. 63/173,943, filed on Apr. 12, 2021.

(51) Int. Cl.
*A61B 1/317* (2006.01)
*A61F 2/46* (2006.01)
*G16H 20/40* (2018.01)

(52) U.S. Cl.
CPC ............... *G06T 7/62* (2017.01); *G16H 20/40* (2018.01); *A61F 2002/4633* (2013.01); *G06T 2207/10016* (2013.01); *G06T 2207/10068* (2013.01); *G06T 2207/20081* (2013.01); *G06T 2207/20084* (2013.01); *G06T 2207/30008* (2013.01); *G06T 2207/30204* (2013.01)

(58) Field of Classification Search
CPC . G06T 2207/10068; G06T 2207/20081; G06T 2207/20084; G06T 2207/30008; G06T 2207/30204; G16H 20/40; A61B 1/000096; A61B 1/317
USPC ........................................................ 382/128
See application file for complete search history.

(56) References Cited

U.S. PATENT DOCUMENTS

| | | |
|---|---|---|
| 6,491,699 B1 | 12/2002 | Henderson et al. |
| 8,860,757 B2 | 10/2014 | Duhamel et al. |
| 9,075,899 B1 | 7/2015 | Reicher |
| 10,130,429 B1 | 11/2018 | Weir |
| 10,169,535 B2 | 1/2019 | Mentis |
| 10,543,046 B2 | 1/2020 | Charron et al. |
| 10,806,325 B2 | 10/2020 | Miller et al. |
| 2003/0181810 A1 | 9/2003 | Murphy et al. |
| 2003/0195883 A1 | 10/2003 | Mojsilovic et al. |
| 2004/0087852 A1 | 5/2004 | Chen |
| 2004/0199404 A1 | 10/2004 | Ripperger et al. |
| 2006/0058616 A1 | 3/2006 | Marquart et al. |
| 2006/0258938 A1 | 11/2006 | Hoffman et al. |
| 2007/0016009 A1 | 1/2007 | Lakin et al. |
| 2007/0116036 A1 | 5/2007 | Moore |
| 2007/0168461 A1 | 7/2007 | Moore |
| 2009/0088897 A1 | 4/2009 | Zhao et al. |
| 2011/0190774 A1 | 8/2011 | Nikolchev et al. |
| 2011/0202370 A1 | 8/2011 | Green, III et al. |
| 2011/0301447 A1 | 12/2011 | Park et al. |
| 2012/0130258 A1 | 5/2012 | Taylor et al. |
| 2012/0289782 A1 | 11/2012 | Viola |
| 2013/0073310 A1 | 3/2013 | Awden |
| 2013/0096373 A1 | 4/2013 | Chabanas et al. |
| 2013/0211232 A1 | 8/2013 | Murphy et al. |
| 2014/0058406 A1 | 2/2014 | Tsekos |
| 2014/0149407 A1 | 5/2014 | Qian et al. |
| 2014/0236159 A1 | 8/2014 | Haider et al. |
| 2014/0267658 A1 | 9/2014 | Speier et al. |
| 2015/0005622 A1 | 1/2015 | Zhao et al. |
| 2015/0221105 A1 | 8/2015 | Tripathi et al. |
| 2016/0000515 A1 | 1/2016 | Sela et al. |
| 2016/0151117 A1 | 6/2016 | Gibbs et al. |
| 2016/0270641 A1 | 9/2016 | Mirza et al. |
| 2016/0378861 A1 | 12/2016 | Eledath et al. |
| 2017/0151022 A1 | 6/2017 | Jascob et al. |
| 2017/0193160 A1 | 7/2017 | Long et al. |
| 2018/0049622 A1 | 2/2018 | Ryan et al. |
| 2018/0071032 A1 | 3/2018 | de Almeida Barreto |
| 2018/0122506 A1 | 5/2018 | Grantcharov et al. |
| 2018/0168740 A1 | 6/2018 | Ryan et al. |
| 2018/0247128 A1 | 8/2018 | Alvi et al. |
| 2018/0249888 A1 | 9/2018 | Kucharski et al. |
| 2018/0366231 A1 | 12/2018 | Wolf et al. |
| 2018/0368656 A1 | 12/2018 | Austin et al. |
| 2019/0069957 A1 | 3/2019 | Barral et al. |
| 2019/0192232 A1 | 6/2019 | Altmann et al. |
| 2019/0209080 A1 | 7/2019 | Gullotti et al. |
| 2019/0311493 A1 | 10/2019 | Hillborg |
| 2019/0362834 A1 | 11/2019 | Venkataraman et al. |
| 2019/0380792 A1 | 12/2019 | Poltaretskyi et al. |
| 2019/0385302 A1 | 12/2019 | Ngo Dinh et al. |
| 2020/0005949 A1 | 1/2020 | Warkentine |
| 2020/0078123 A1 | 3/2020 | Venkataraman et al. |
| 2020/0107002 A1 | 4/2020 | Casas |
| 2020/0197098 A1 | 6/2020 | Chopra et al. |
| 2020/0210769 A1 | 7/2020 | Hou et al. |
| 2020/0211720 A1 | 7/2020 | Goldberg |
| 2020/0237452 A1 | 7/2020 | Wolf et al. |
| 2020/0265273 A1 | 8/2020 | Wei et al. |
| 2021/0059758 A1 | 3/2021 | Avendi et al. |
| 2021/0128244 A1 | 5/2021 | Couture et al. |
| 2021/0196382 A1 | 7/2021 | Mumaw et al. |
| 2021/0196398 A1 | 7/2021 | Ye et al. |
| 2021/0256719 A1 | 8/2021 | Hufford et al. |
| 2021/0298869 A1 | 9/2021 | Wolf et al. |
| 2021/0307841 A1 | 10/2021 | Buch et al. |
| 2021/0338331 A1 | 11/2021 | Quaid, III |
| 2021/0338342 A1 | 11/2021 | Abhari et al. |
| 2021/0350934 A1 | 11/2021 | Kinsey et al. |
| 2021/0390693 A1 | 12/2021 | Zhang et al. |
| 2022/0087746 A1 | 3/2022 | Lang |
| 2022/0207896 A1 | 6/2022 | Fouts et al. |
| 2023/0190136 A1 | 6/2023 | Kumar et al. |
| 2023/0200625 A1 | 6/2023 | Kumar et al. |
| 2023/0245753 A1 | 8/2023 | Kumar et al. |
| 2023/0263573 A1 | 8/2023 | Bakhishev et al. |
| 2024/0082019 A1 | 3/2024 | Jonelagadda |

FOREIGN PATENT DOCUMENTS

| | | |
|---|---|---|
| JP | 2013509273 | 3/2013 |
| JP | 2013513462 A | 4/2013 |
| JP | 2016506260 A | 3/2016 |
| JP | 2018537155 A | 12/2018 |
| JP | 2019508072 A | 3/2019 |
| KR | 10-1049507 B1 | 7/2011 |
| WO | WO00/64367 A1 | 11/2000 |
| WO | WO2004/095359 A2 | 11/2004 |
| WO | WO2017002388 A1 | 1/2017 |
| WO | WO2019/049503 A1 | 3/2019 |
| WO | WO2019/050612 A1 | 3/2019 |
| WO | WO2019/133071 A1 | 7/2019 |
| WO | WO2020/017212 A1 | 1/2020 |
| WO | WO2020035852 A2 | 2/2020 |
| WO | WO2020/047051 A1 | 3/2020 |
| WO | WO2021/144230 A1 | 7/2021 |
| WO | WO2021/263174 A1 | 12/2021 |
| WO | WO2022/197550 A1 | 9/2022 |
| WO | WO2023/168306 A2 | 9/2023 |

OTHER PUBLICATIONS

Buslaev et al.; Albumentations: Fast and flexible image augmentations; Information; 11(2); 125; doi:10.33990/info11020125; 20 pages; Feb. 2020.

Cheng et al.; Deep learning assisted robotic magnetic anchored and guided endoscope for real-time instrument tracking; IEEE Robotics and Automation Letters; 6(2); pp. 3979-3986; Mar. 17, 2021.

Demirel; A hierarchical task analysis of shoulder arthroscopy for a virtual arthroscopic tear diagnosis and evaluation platform (VATDEP); The International Journal of Medical Robotics and Computer Assisted Surgery; 13(3):e1799;29 pages; (Author Manuscript); Sep. 2017.

Hertel; Trust and Behavioral Intention Toward Generative Adversarial Network (GAN)-Derived Avatar Healthcare Provider (HCP) in Simulated Telehealth Setting. The Florida State University; 2021; retrieved from the internet (https://diginole.lib.fsu.edu/islandora/object/fsu:803248/datastream/PDF/view); on Nov. 3, 2023.

Jonmohamadi et al.; Automatic segmentation of multiple structures in knee arthroscopy using deep learning; IEEE Access; vol. 8; pp. 51853-51861; Mar. 10, 2002.

(56) References Cited

OTHER PUBLICATIONS

Jung et al.; Navigation-assisted anchor insertion in shoulder arthroscopy: a validity study; BMC Musculoskeletal Disorders; 21(1); pp. 1-9; Dec. 2020.
Mildenhall et al.; NERF: representing scenes as neural radiance fields for view synthesis; Communications of the ACM; 65(1); pp. 99-106; Dec. 2021.
Ruiz U.S. Appl. No. 18/555,248 entitled "Systems and methods for AI-assisted medical image annotation," filed Oct. 12, 2023.
Jonelagadda et al.; U.S. Appl. No. 18/692,794 entitled "System and method for searching and presenting surgical images," filed Mar. 15, 2024.
Jonelagadda et al.; U.S. Appl. No. 18/693,945 entitled "System and method for computer-assisted surgery," filed Mar. 20, 2024.
Barban et al. U.S. Appl. No. 18/745,993 entitled "Back table optimization using real time surgical activity recognition," filed Jun. 17, 2024.
Petscharnig et al.; Binary convolutional neural network features off-the-shelf for image to video linking in endoscopic multimedia databases; Multimedia Tools and Applications; 77(21); pp. 28817-28842; Nov. 2018.
Petscharnig; Semi-automatic retrieval of relevant segments from laparoscopic surgery videos; InProceedings of the 2017 ACM on International Conference on Multimedia Retrieval; pp. 484-488; Jun. 6, 2017.
Schoeffmann et al.; Content-based retrieval in videos from laparoscopic surgery; InMedical Imaging 2016: Image-Guided Procedures, Robotic Interventions, and Modeling; SPIE; vol. 9786; pp. 562-571; Mar. 18, 2016.
Wei et al.; Real-time visual servoing for laparoscopic surgery; Controlling robot motion with color image segmentation; IEEE Engineering in Medicine and Biology Magazine: 16(1); pp. 40-45; Jan. 1997.

SYSTEMS AND METHODS FOR USING IMAGE ANALYSIS TO GUIDE A SURGICAL PROCEDURE

CLAIM OF PRIORITY

This patent application is a continuation of U.S. patent application Ser. No. 18/555,252, titled "SYSTEMS AND METHODS FOR USING IMAGE ANALYSIS IN SUPERIOR CAPSULE RECONSTRUCTION," filed Oct. 12, 2023, now U.S. Pat. No. 12,004,966, which is a national phase application under 35 U.S.C. 371 of International Patent Application No. PCT/US2022/024503, titled "SYSTEMS AND METHODS FOR USING IMAGE ANALYSIS IN SUPERIOR CAPSULE RECONSTRUCTION," filed on Apr. 12, 2022, now International Publication No. WO 2022/221341, which claims priority to U.S. Provisional Patent Application No. 63/173,943, titled "SYSTEMS AND METHODS FOR USING IMAGE ANALYSIS IN SUPERIOR CAPSULE RECONSTRUCTION," filed on Apr. 12, 2021 and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Rotator cuff tears can be a challenging problem for arthroscopists in the perioperative setting. Superior capsular reconstruction (SCR) is an advancing treatment option for patients with rotator cuff tears that are neither amenable to primary repair nor ideal for arthroplasty. However it may be particularly difficult to perform SCR, particularly in patients whose anatomy may be hard to access and image. Further imaging may strongly impact favorable surgical outcomes. Imaging may be critical and/or helpful in performing an SCR procedure as well interpreting patient outcomes and determining post-procedure follow-up care following a surgery. Current methods for imaging and interpreting SCR procedures are severely lacking, particularly in accurately estimating locations, dimensions and distances of anatomical and surgical components.

SUMMARY OF THE DISCLOSURE

Described herein are apparatuses (e.g., systems, devices, etc., including software) and methods for assisting, guiding and/or reviewing surgical reconstruction of an injury to a patient's shoulder.

For example, described herein are computer-implemented methods for guiding surgical reconstructive of an injury to a patient's shoulder joint, the methods comprising: receiving imaging data contained in a video stream (e.g., captured by an in-situ imaging device) that traverses a treatment site in a shoulder area of the patient; processing image data from an-situ imaging device; analyzing the image data to (i) detect image data that depicts a set of anchor structures in the treatment site, (ii) determine an orientation attribute of each anchor structure of the set with respect to a reference; and (iii) determine a respective scale factor for one or more portions of image data that depict each anchor structure of the set, the respective scale factor of each portion of the image data reflecting a distortion in size of that portion of the image data with respect to a reference scale; determining geometric information for at least a portion of the treatment site where the set of anchor structures are located; and calculating at least a first measurement that represents a physical span between a pair of anchor structures of the set, based at least in part on the orientation attribute of each anchor structure of the set, the respective scale factor of each portion of the image data, and the determined geometric information.

In general, these methods may include calculating at second measurement that represents a physical span between a second pair of anchor structures of the set. The first and second measurements may be used to determine at least one of location or dimensional information of a graft placed in the treatment site. The location information may be a position of the graft at the treatment site. The position of the graft may be with respect to a location of at least one of anchor structures. The dimensional information may be at least one of a size, width or area of the graft.

In any of these methods, at least one of the location or dimensional information may be configured to optimize a postoperative kinematic function of the patient's shoulder. For example, the post-operative kinematic function may include at least one of a stability or range of motion of the patient's rotator cuff or shoulder. In some examples, the post-operative kinematic function may be that of a glenohumeral junction.

Any of these methods may include analyzing the image data to determine anatomical characteristics of the treatment site; and determining the reference for the orientation attribute of the set of implant structures based at least in part on the determined anatomical characteristics.

The injury may be a torn rotator cuff and the surgical reconstruction is reconstruction of the patient's superior capsule. In some examples the image data includes processing multiple frames of the video stream; and analyzing the image data includes identifying one or more markers for the target site in a first frame of the video feed and tracking the one or more markers to one or more subsequent frames of the video feed. The one or more markers may correspond to locations for the anchor structures. In any of these methods, the imaging device may be an arthroscope. The image data may be processed using at least one trained computer algorithm. For example, processing may comprise identifying one or more elements in the image data, wherein said one or more elements comprise one or more of an anatomical structure, a surgical tool, or a pathology. In some examples processing further comprises: receiving an indication from an operator to select one or more of a plurality of points or an area in said video stream; calculating one or more measurements for said selected area in said video stream; wherein said one or more measurements comprise one or more of a length, a surface area, a circumference, or a volume; and displaying said measurements on a displaying device intraoperatively to be used by an operator during said arthroscopic procedure. The least one trained computer algorithm may comprise one or more trained machine learning algorithms, one or more trained deep learning algorithms, or a combination of both. In some examples the image data is processed using one or more processing modules. The one or more processing modules may comprise at least one of a video stream decomposition module, a tool recognition module, a tooltip reference sizing module, an anatomy recognition module, a tool tracking module, a landmark establishment module, a distance aggregator module, a video blend module, a pathology detection module, a pathology sizing module, or a radiology imaging module. The one or more processing modules may comprise trained machine learning algorithms. For example, the trained machine learning algorithm may be a neural network.

In some examples the processing module is a video stream decomposition module that decomposes said video stream into a series of images. For example, the series of images may be stored in a memory device, such as, but not limited to a non-volatile memory device or a flash drive. In some examples the memory device may be a volatile-memory device, a RAM device or an SRAM device.

Any of the methods described herein may be implemented as a non-transitory computer-readable medium including contents that are configured to cause one or more processors to perform the method, for example, the method of: receiving imaging data contained in a video stream captured by an in-situ imaging device that traverses a treatment site in a shoulder area of the patient; processing image data from an-situ imaging device; analyzing the image data to (i) detect image data that depicts a set of anchor structures in the treatment site, (ii) determine an orientation attribute of each anchor structure of the set with respect to a reference; and (iii) determine a respective scale factor for one or more portions of image data that depict each anchor structure of the set, the respective scale factor of each portion of the image data reflecting a distortion in size of that portion of the image data with respect to a reference scale; determining geometric information for at least a portion of the treatment site where the set of anchor structures are located; and calculating at least a first measurement that represents a physical span between a pair of anchor structures of the set, based at least in part on the orientation attribute of each anchor structure of the set, the respective scale factor of each portion of the image data, and the determined geometric information.

Also described are systems including one or more processors and a memory coupled to the one or more processors, the memory storing computer-program instructions, that, when executed by the one or more processors, perform any of the computer-implemented methods described herein.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative examples, and the accompanying drawings of which.

DETAILED DESCRIPTION

Figure 1:
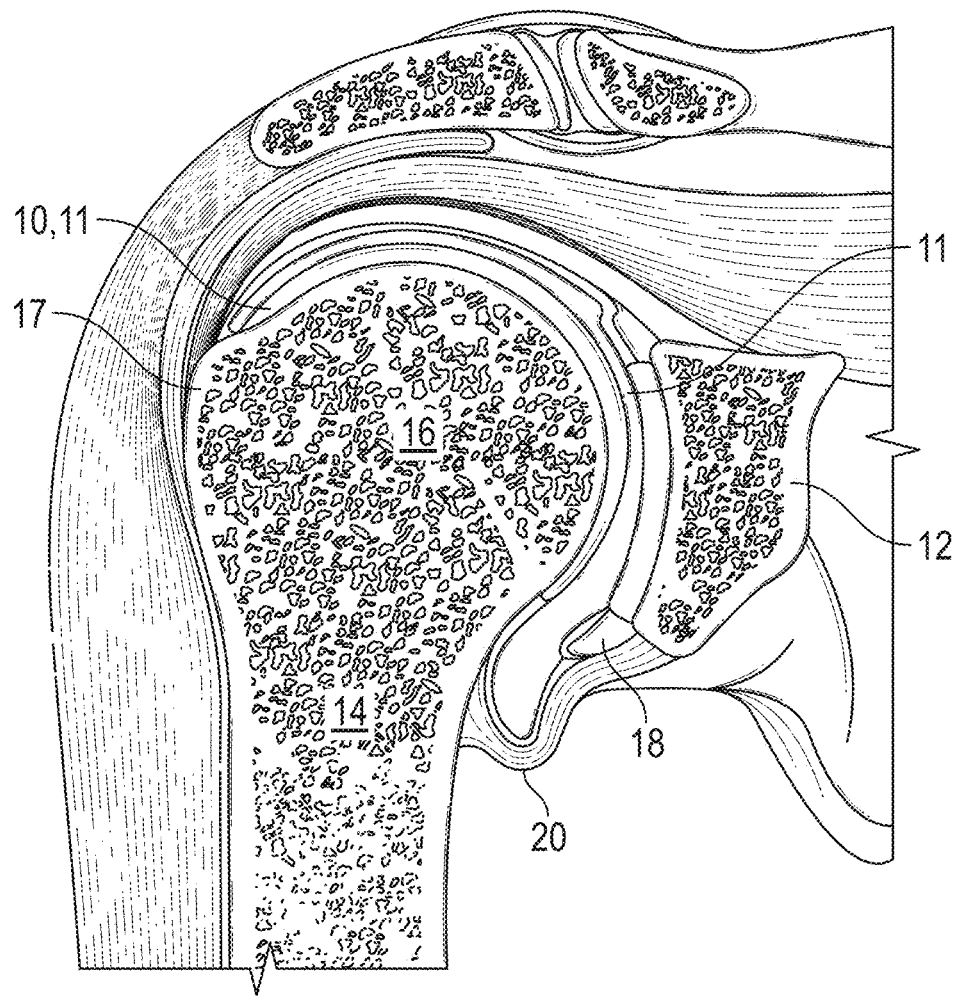
FIG. 1 illustrates a glenohumeral joint of a shoulder of the human musculoskeletal system.

Described herein are apparatuses (e.g., devices, systems, etc., including software, firmware and hardware) and methods to assist diagnostic and interventional medical procedures using image analysis. More particularly, the methods and apparatuses described herein may relate to image analysis to guide and assist with arthroscopic-based superior capsule reconstruction or SCR.

Superior capsule reconstruction (SCR) is a recently developed treatment option for patients with posterosuperior rotator cuff tears. It has produced improved clinical outcomes for patients with these types of rotator cuff tears. SCR techniques stabilize the tear using a graft that is placed in the rotator cuff area (e.g., from the superior glenoid to the greater tuberosity) to stabilize the head of the humeral bone. While SCR has been shown to be effective in repairing a torn rotator cuff and in turn, restoring the function of the shoulder, it requires considerable skill to be performed properly including skill in sizing and placement of the graft. Complicating matters is the fact that tissue measurements in the treatment area which are used for sizing and graft placement must be done using an externally placed measurement device that is not always accurate and can lead to errors in sizing and placement of the graft. Thus, there is a need for improved tissue measurement techniques for an SCR procedure.

Computational methods such as machine learning and deep learning algorithms are being developed with increasing sophistication to analyze image data in various context and applications. In recent years, Artificial Intelligence has begun to be developed to be used to process images to recognize features of a human face as well as different anatomical structures in a human body.

AI tools can be used to automatically recognize an anatomical feature to help assist during a medical procedure. image or language processing to gather and process information generated in a medical procedure such a surgical procedure.

According to some examples, systems and methods are provided for using Artificial Intelligence to guide and assist with arthroscopic-based techniques for reconstructing an injured and/or unstable joint such as those resulting from a torn rotator cuff. Many examples provide systems and methods for using computer implemented AI algorithms to guide and assist with arthroscopic-based techniques for reconstructing damaged anatomical structures in the patient's shoulder area such as a superior capsule which results from a severely torn rotator cuff. Examples of the method and apparatuses described herein are particularly useful for optimizing or otherwise improving the post-operative kinematic function (including stability and range of motion) of a torn rotator cuff.

In a first aspect the method and apparatuses described herein provides a computer-implemented method for guiding surgical reconstruction of an injury to a patient's shoulder joint such as the those resulting from a torn rotator cuff or related injury. The method includes receiving imaging data contained in a video stream captured by an arthroscope or other in-situ imaging device that traverses or otherwise is positioned at a treatment site in a shoulder area of the patient. The image data from the imaging device is processed and then analyzed using one or more computer modules which may employ machine learning algorithms.

Specifically the image data is analyzed to: (i) detect image data that depicts a set of anchor structures in the treatment site, (ii) determine an orientation attribute of each anchor structure of the set with respect to a reference; and (iii) determine a respective scale factor for one or more portions of image data that depict each anchor structure of the set, the respective scale factor of each portion of the image data reflecting a distortion in size of that portion of the image data with respect to a reference scale. Geometric information such as size and shape is determined for at least a portion of the treatment site where the set of anchor structures are located. Then at least a first measurement is calculated which represents a physical span between a pair of anchor structures of the set, the calculation being based at least in part on the orientation attribute of each anchor structure of the set, the respective scale factor of each portion of the image data, and the determined geometric information. A second measurement that represents a physical span between a second pair of anchor structures of the set may be similarly calculated. The first and second measurements may then be used to determine location or dimensional information of a graft placed in the treatment site as part of the reconstructive procedure. The location information may correspond to a desired anchored position of the graft at the treatment site including with respect to a location of at least one of one or more of the anchor structures. For example, the location information may include a specific location and orientation with respect to the superior glenoid and the greater tuberosity of the shoulder area. The dimensional information may correspond to at least one of a size, width or area of the graft, desirably all three.

In various examples, one or both of the location and dimensional information allows for optimization and/or improved postoperative function including kinematic function of the shoulder including that of the glenohumeral junction. The improved kinematic function can include improved joint stability, range of motion with reduced amounts of pain and inflammation. In this way examples of the method and apparatuses described herein result in improved clinical outcomes for arthroscopic procedures.

Examples of the method and apparatuses described herein provide systems and methods for using Artificial Intelligence to guide and assist with arthroscopic-based techniques for reconstructing an injured and/or unstable joint such as those resulting from a torn rotator cuff or other torn or damaged tissue. Many of the examples described herein may provide systems and methods for using computer implemented AI algorithms such as machine learning algorithms to guide and assist with arthroscopic-based techniques for reconstructing damaged anatomical structures in the patient's shoulder area, for example, techniques for reconstructing a superior capsule resulting from a severely torn rotator cuff. As used herein the term "about" means within 10% of a stated value including those for a measurement, characteristic, parameter or property and more preferably within 5% of such a stated value. Similarly, the term "substantially" means with 10% of a stated property, condition, or state, and more preferably within 5% of such a property, condition or state.

For purposes of background information, a summary will now be presented of the anatomy of the shoulder joint and the procedure for reconstructing a superior capsule using a graft. FIG. 1 is a prior art illustration of a glenohumeral joint of a shoulder 10 of the human musculoskeletal system. The joint 10 includes multiple bones including a scapula 12 and a humerus 14 having a humeral head 16 and ridge on the head 17 known as the greater tuberosity (aka greater tubercle). Some of these bones articulate relative to one another. For example, the joint 10 includes a ball and socket joint 11 formed between humeral head 16 and a glenoid 18, which is a cup-like recession of the scapula 12 configured to receive the head 16.

A capsule 20 generally covers the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 14 and the glenoid 18), the capsule 20, or other surrounding muscles, tendons and/or ligaments. In particular, when there is an irreparable tear in the rotator cuff, the joint can become unstable in part due to an underlying tear in capsule 20 which typically accompanies a torn rotator cuff. This instability can result in both pain and reduced function of the shoulder. This instability can be corrected by surgical reconstruction of the superior portion of capsule 20, also referred to as the superior capsule 20.

In one or more examples of a procedure for reconstruction of the super capsule (also described herein as superior capsule reconstruction or SCR), the surgeon prepares the area (e.g., by clearing way torn cartilage or other tissue), drills anchors and then fastens a graft across the humeral head and the glenoid to the anchors. The graft can be an autograft or allograft. Auto grafts are taken from the patient's own tissue such as a long head. Allografts are taken from tissue of another person (typically a cadaver) and may correspond to a tibialis tendon, hamstring, or dermal allograft which may be combination of synthetic and human tissue. A well-placed graft stabilizes the shoulder joint by arresting the upward movement of the humeral head and lets the arm rotate at the shoulder joint. Typically, the surgeon accesses the injured region of the patient's shoulder area from the lateral portal, i.e., viewed from the side, above the humeral head.

A typical SCR procedure consists of first placing four anchors, two on the glenoid and two on the top of the tuberosity. Given the orientation of the portal, the anchors on the tuberosity are closer to the surgeon and the anchors on the glenoid are further away. Once these anchors are placed and sutures are run through them, the surgeon measures the distance between the anchors with the patient's arm placed at location recommended by the company that manufactures the anchors. A suitably sized graft is selected and trimmed down. Suture holes are then drilled at specific locations on the graft in order to provide openings through which sutures are threaded through and then used to attach the graft to the anchors. As stated below, the suture holes of the graft should be positioned to match the precise locations of the sutures in the shoulder joint.

Proper sizing of the graft and the precise placement of the holes is important for the success of this procedure. In particular, if the graft is too loose, the shoulder joint is not stable and the humeral head's upward movement is not arrested properly. If the graft is too tight, it restricts normal movement of the arm. Complicating the problem of sizing is the fact that anatomical constraints limit the amount of room a surgeon has to properly place measuring tools, and the surgeon has limited time to make such measurements. Examples of the method and apparatuses described herein provide solutions to these problems by providing AI systems which use the video feed from an arthroscope or other in situ medical imaging device to perform the measurement digitally for example using image recognition and analysis algorithms.

Examples of the method and apparatuses described herein provide an AI-based system for aiding and/or assisting with SCR surgery where the system comprises a computer and one or more software modules (herein modules) containing algorithms operable on the computer which analyze one more frames/images from a video stream from an arthroscope (or other imaging device used during the procedure) and perform a series of computations to determine geometric and dimensional attributes of the graft used in an SCR procedure. Such attributes can include one or more of the shapes and dimensions of the graft was well the locations of points known as anchor points where the graft is attached to tissue (typically by anchors implanted into selected bones of the joint such as the humeral head or glenoid). The computer system includes one or more processors (e.g., microprocessors, ASIC, etc.) or other logic resources which implement/execute the AI-algorithms. Typically, the processors will include at least one graphical processing unit or GPU such as those manufactured by the NVIDIA corporation. The computer will also include various memory devices such as RAM, DRAM, SRAM or other volatile memory device as well as non-volatile memory devices device such as a flash drive which is configured to store one or more images (either from the video stream or generated by modules/algorithms of the method and apparatuses described herein) for processing and subsequent display. The computer can also be configured to be operably coupled to a flash drive (or other memory device) by means of a port such as a USB port for storing images and other information on the flash drive. In still other examples, the computer can be configured to be operably coupled to a network such as the Internet for uploading the images and other information in the Cloud or another computer device operably coupled to the network/Internet.

Figure 2:
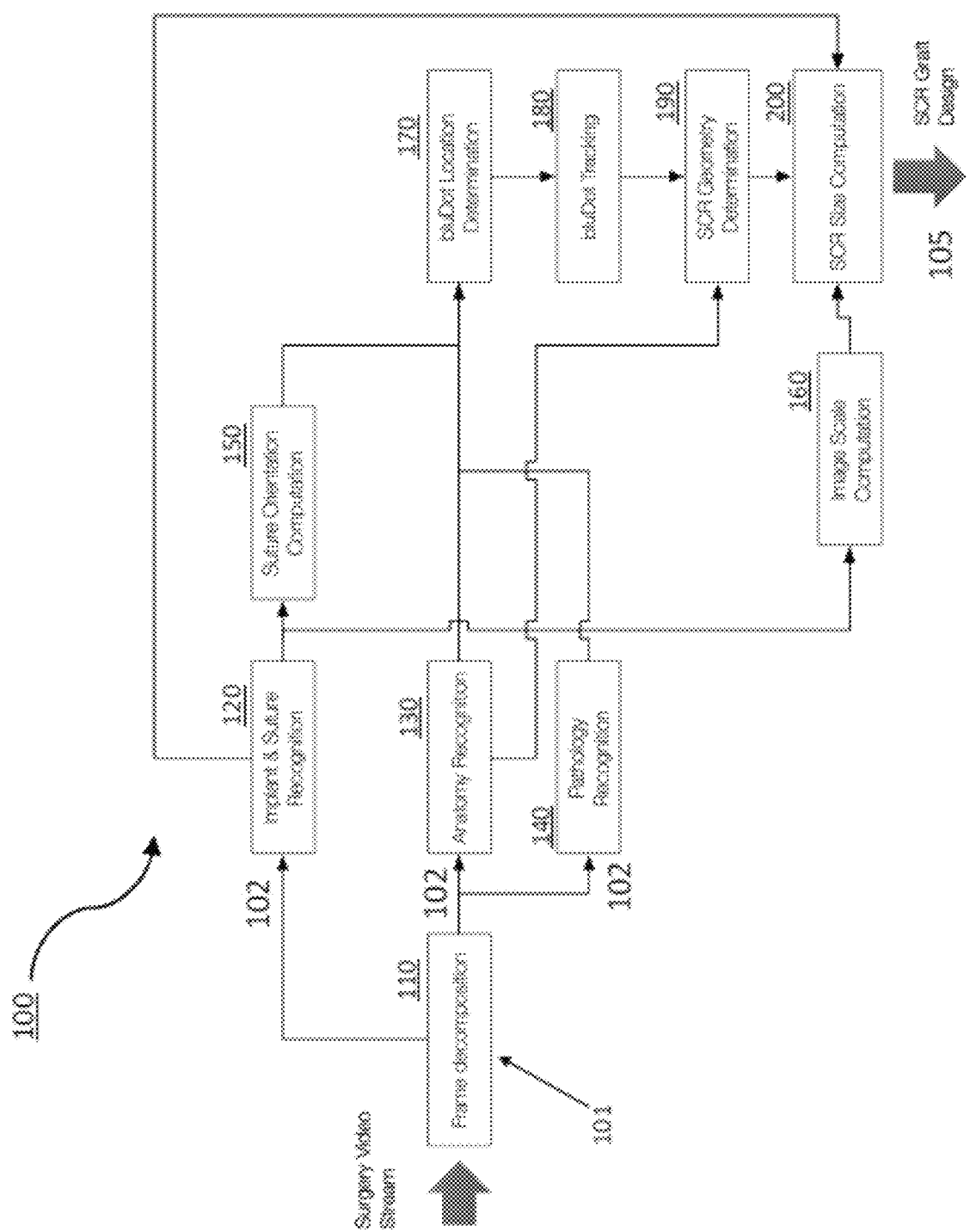
FIGS. 2 and 3 schematically illustrates one example of a graph design system that can include a suture orientation component that includes one or more processes to identify an orientation of the individual sutures used with each implant of the patient.

FIG. 2 illustrates a graph design system for determining an SCR graft design, using image data obtained from a patient. In some examples, a graph design system 100 is implemented to generate a design output 105 for a patient-specific graft for use in an SCR procedure. Accordingly, in some examples, the graph design system 100 can operate in a real-time environment to generate the design output, using, for example, video or other image data captured by a surgical camera during an SCR procedure performed on a patient. In the course of the SCR procedure, the physician sutures a number of implants (or anchors) about the patient's shoulder (e.g., on or near the glenoid and tuberosity of the humerus). The implants are then used to affix and secure the graft that is formed for the patient. As described with examples, the graph design system 100 generates a design output 105 to enable a graft to be constructed to the specific dimensions and design constraints required for the SCR procedure.

With reference to an example of FIG. 2, examples provide for graph design system 100 to include a video decomposition component 110, an implant recognition component 120, an anatomy recognition component 130, and a pathology recognition component 140. The video decomposition component 110 can include one or more processes that decompose a video feed captured from a surgical procedure into frames, and further select individual frames for image analysis. The video decomposition component 110 supplies image data 102 (e.g., frames of a video feed) to each of the implant recognition component 120, the anatomy recognition component 130, and the pathology recognition component 140. Accordingly, in generating the image data 102, the graph design system 100 can utilize multiple image recognition processes, as described with examples.

The implant recognition component 120 can process image data 102 to recognize implants a physician makes in the relevant anatomy of the patient. The anatomy and pathology recognition components 130, 140 includes processes that recognize anatomical structures of the shoulder and the tissue pathology to be repaired (e.g., tears in one or more of the rotator-cuffs, bursa). The anatomical structures of the shoulder that are recognized (which are those from the bursal view) typically include one or more of the glenoid, capsule, head of the humerus, bursa, the greater tuberosity, as well as structures or conditions which may be visible from within a hole formed in the bursa.

The implant recognition component 120 can recognize portions of the image data 102 which depict implants, where each implant corresponds to an anchor that is sutured in place.

Accordingly, each implant may be depicted in the image data 102 as an elongated shape that terminates at an end region, reflecting the presence of sutures that terminate at an end-region or anchor point. The graph design system 100 can implement one or more processes that utilize an output of the implant recognition component 120 and the anatomy recognition component 130 to detect the respective anchor point of each implant that the physician makes during the procedure. In examples, each identified anchor point can reflect a point of measurement for determining one or more physical measurements or features (e.g., pre-made holes) of the graft that is to be used for the particular patient.

Figure 3:
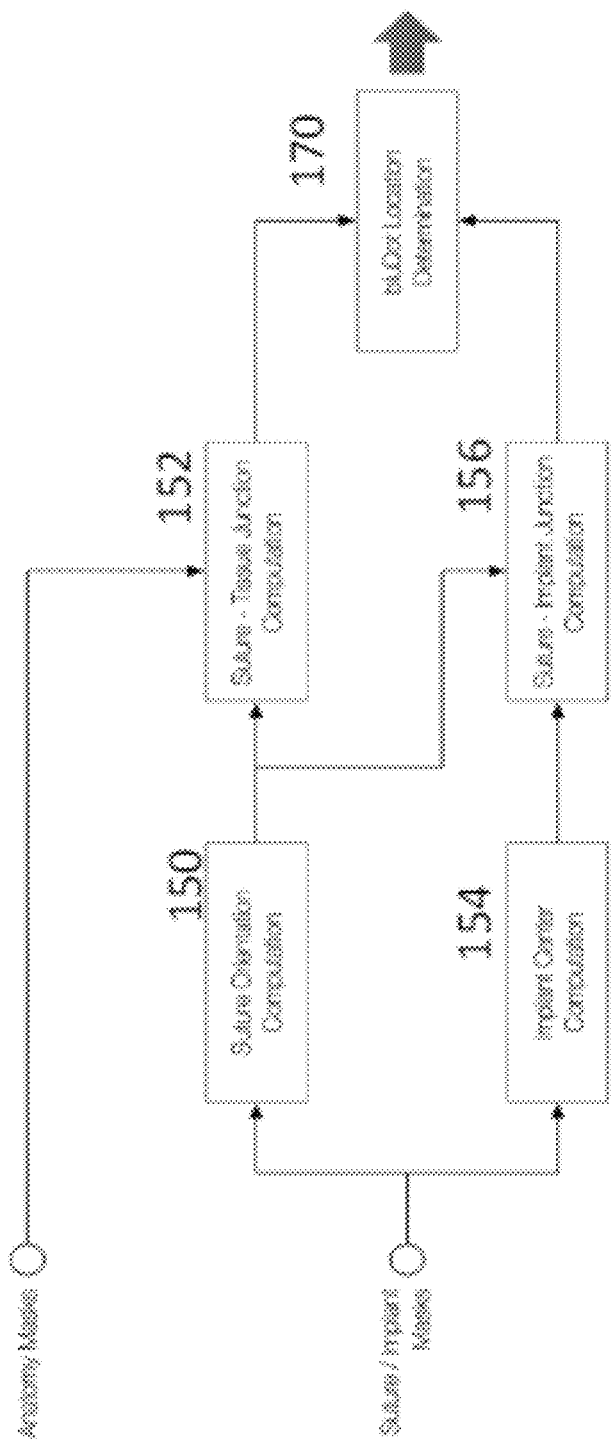

With reference to FIG. 2 and FIG. 3, the graph design system 100 can include a suture orientation component 150 that includes one or more processes to identify an orientation of the individual sutures used with each implant of the patient. The sutures of each implant can be substantially linear, so as to be characterized by a length and an orientation angle or primary axis (as determined with respect to predefined frame of reference). To determine the anchor, point of each implant, the suture orientation component 150 includes suture-tissue junction logic 152 which identifies the boundary of the depicted sutures for each implant. The boundary can be determined based in part on, for example, a comparison of pixel values along a segment of the image where a suture is depicted, where the comparison identifies contrasting brightness, shading and/or hue values for adjacent pixels or pixel clusters.

With further reference to FIG. 3, as an addition or variation, the graph design system 100 can include implant center computation logic 154 to determine the center of each implant. The implant center computation logic 154 can utilize input representing the orientation of each implant, separate from the sutures. From the determined center, the graph design system 100 can implement implant-suture logic 156 that utilizes the determined orientation of the sutures to identify a juncture between a respective structure of the implants and the sutures. As shown by an example of FIG. 4 and FIG. 5, the graph design system 100 can segment or otherwise delineate the portion of the image data depicting the sutures, with the end regions being determined by shape and/or the presence of the implant separate from the suture.

With further reference to FIG. 2, the graph design system 100 can also include a marker component 170 that creates a visual marker (e.g., blue dot) on the portion of the image data 102 where the identified anchor points of the implant are located. The location of the visual marker may then be tracked. In particular, the graph design system 100 can include a marker tracking component 180 to track and update the marker position (reflecting the location of the sutured implant endpoint) over successive frames of a video feed. As additional implants are recognized and their respective anchor points are identified, the marker component 170 and the marker tracking component 180 combine to mark respective portions of the image data 102 where the respective anchor points of the implants are deemed to reside.

In examples, the graph design system 100 includes a geometry determination component 190 that utilizes the location of the visual markers, as generated by the marker component 170, in conjunction with an output of the anatomy recognition component 130 (e.g., anatomy mask for relevant patient anatomy) to determine which of the anchor points are on the glenoid and which are on the humeral head (typically on the greater tuberosity). As an addition or variation, the geometry determination component 190 can be configured to determine, which of the anchor points are anterior and which are posterior. In one or more examples, the geometry determination component 190 assumes that the SCR procedure is performed from the lateral portal. Accordingly, in such examples, the anchor point (or anchor point) on the glenoid to the left in the surgical field of view would be the anterior anchor point on the glenoid, the anchor points to the right on the glenoid would be the posterior anchor point on the glenoid, and so on. The geometry determination component 190 can assign appropriate labels to each of the anchor points (e.g., anterior glenoid, posterior glenoid, etc.). In some examples, the geometry determination component 190 may also identify the presence of contours or surface features that can affect the manner in which the implanted graft spans the affected area.

Additionally, in examples, the graph design system 100 can implementing an image scaling component 160 that determines a scaling factor for the processed image data. For example, the size of the recognized objects of the image data (e.g., such as the anchors, the anatomical regions, etc.) may be impacted by the type, mode (or setting), position and orientation of the camera device used to acquire the image data. The image scaling component 160 can utilize reference data to determine, for example, one or more scaling factors for the image data.

The image scaling component 160 may determine the reference data from, for example, the camera setting, manual input (e.g., data identifying a relevant positioning of the camera with respect to the anatomy) and/or with reference to objects or features that appear with the image data and for which a physical dimension is known.

The graph design system 100 can further include a size computation component 200. The size computation component 200 can compute the location of the anchor points in terms of pixels which depict the respective implants. The pixels are then desirably converted to a specific dimensional location and/or size (e.g., position or dimension of an anchor point). In various examples the conversion from pixels in dimensional location/size can be done using methods described in U.S. Provisional Patent Application Ser. Nos. 63/030,731 and 63/143,390, filed Apr. 27, 2020 and Jan. 29, 2021 respectively which are fully incorporated herein for all purposes. For the sake of calibration, the system assumes that standard sized 2 mm sutures are used. Surgeons are known to use standardized sutures. However, examples of a computer system using the SCR Size Computation or other module described herein can be configured to allow for alternate sized sutures to be used (e.g., 1, 3 mm, 5 mm, etc.). In particular examples, the system/modules can be configured to perform a measurement of the suture size or can include a prompt for the surgeon to input the suture size. In one or more implementations, the prompt may be overlayed on the screen displaying the video and the input may be done by input device such as a keyboard, mouse, computer touch screen, portable wireless device (e.g., cell phone or tablet device) or the like operably connected to the computer system which is implementing one or more of the modules described herein.

As described with an example of FIG. 2 and FIG. 3, the graph design system 100 determines a design output 105 for the graft, with the design output 105 specifying parametric information that defines, for example, a geometry for a patient's graft. In examples, the design output 105 may be in the form of an image overlay on a video stream of the arthroscopic procedure, and/or as a still image or print out. In some examples, the design output 105 may be in the form of a generated image of the graft with the dimensions labeled on the image as well as specific labelling of the anchor points (e.g., anterior glenoid, posterior glenoid, etc.). Still further, the design output 105 can provide display values for configuration parameters of the graft (e.g., numeric dimensions of the graft). The design output 105 can, for example, identify parametric information, such as a physical span between one or more pairs of the anchor end regions; (ii) identify and account for a curvature of the patient's anatomy where the graft is to be received; and/or (iii) identify locations and dimensions of holes that are to be formed in the graft (e.g., coinciding with the position of the end regions).

Figure 4:
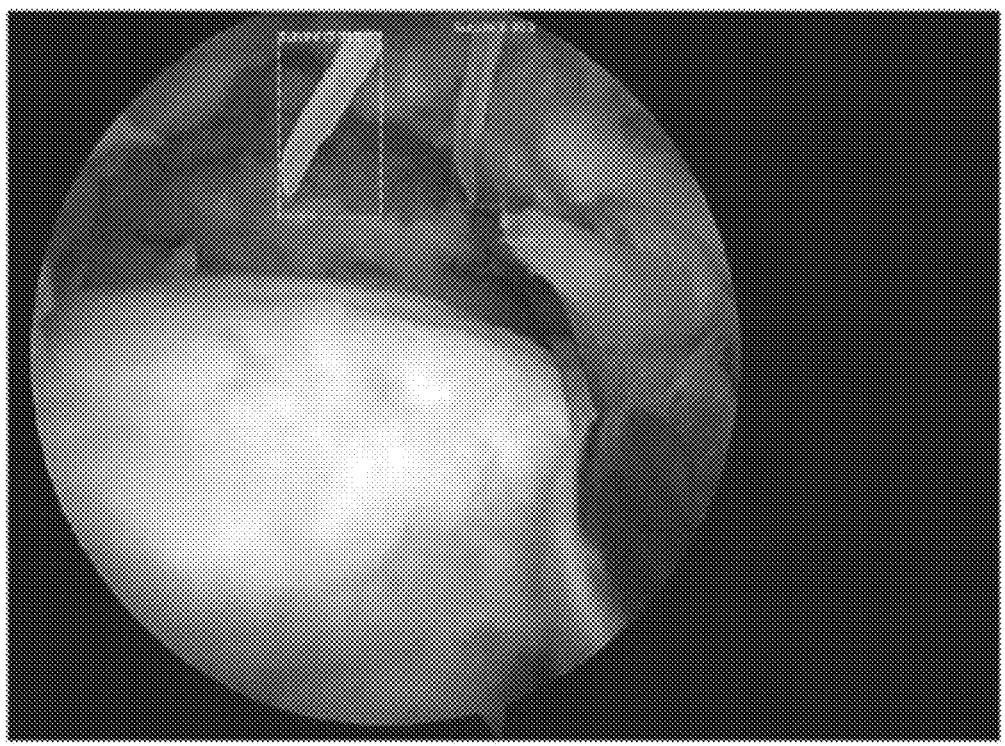
FIG. 4 is an example of an image taken with an apparatus as described herein.
Figure 5:
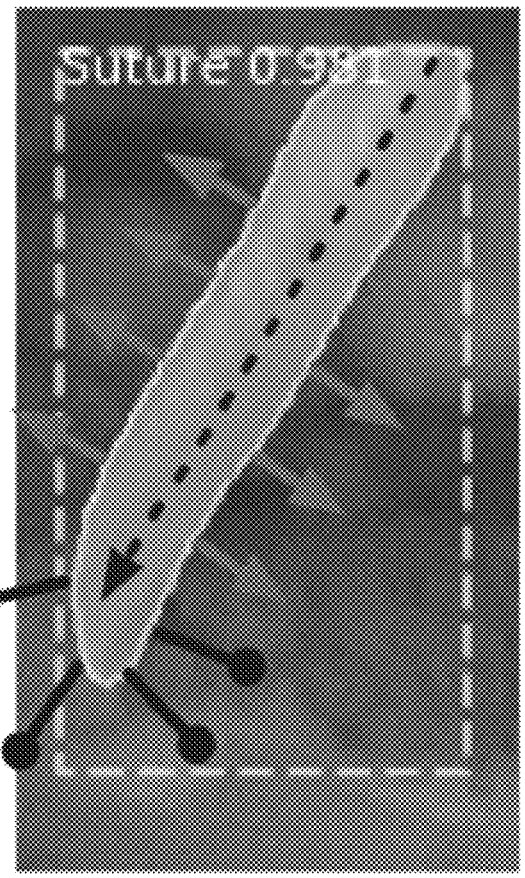
FIG. 5 is an example of an image taken with an apparatus as described herein.
Figure 6:
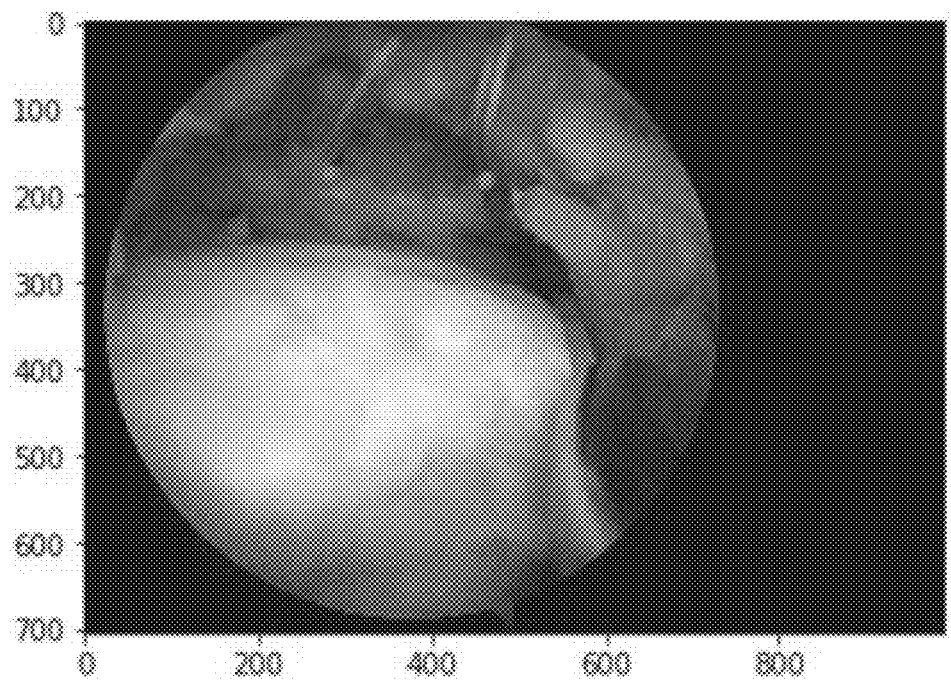
FIG. 6 is an example of an image used with the apparatuses and methods described herein.

FIGS. 4-6 illustrate processed images in accordance with one or more examples. FIG. 4 illustrates an image (e.g., as captured by a video frame) in which a pair of implants are recognized and delineated from a remainder of the image (e.g., each implant displayed as dashed rectangle, in green or red). From the recognized implant, a primary axis of the suture can be computed. FIG. 5 illustrates further analysis performed on an image to identify a portion of the recognized implant that coincides with an anchor point, separate from a portion of the implant reflecting the extension of a suture. The graph design system 100 can implement the suture tissue computation logic to identify pixels on the suture/tissue boundary along the length of the recognized implant and based on the orientation and length of the implant, select the portion of the depicted implant that is an end-region (or anchor point).

With specific reference to FIGS. 5 and 6, in particular examples of suture selection algorithms, the principal direction of a given suture is used to narrow the region of interest or ROI used to select a particular suture or section of a particular suture including that portion entering tissue at an anchor point (i.e., the point where the graft will be attached to the anchor). A set of pixels closest to the end of the suture, at the junction of the suture/tissue boundary, along the principal direction of the suture, is determined to be the intended location of the anchor point. For example, the landmark placement algorithms described in PCT application PCT/US21/27000, (which is herein incorporated by reference for all purposes) may be used to place a blue dot or other landmark at this location and tracking of that point is performed on subsequent frames. In one or more examples, the size of the ROI is configurable and is calibrated to match the magnification of the scope used during the procedure. For typical arthroscopes, the ROI is set at about 16 pixels across. However, in alternative or additional examples, larger and smaller pixel sizes are also contemplated. FIG. 6, shows an example of an output the "bluDot" Location Determination module with the suture-tissue boundary points (i.e., where the suture is anchored in tissue, aka the anchor point) shown in red.

Figure 7:
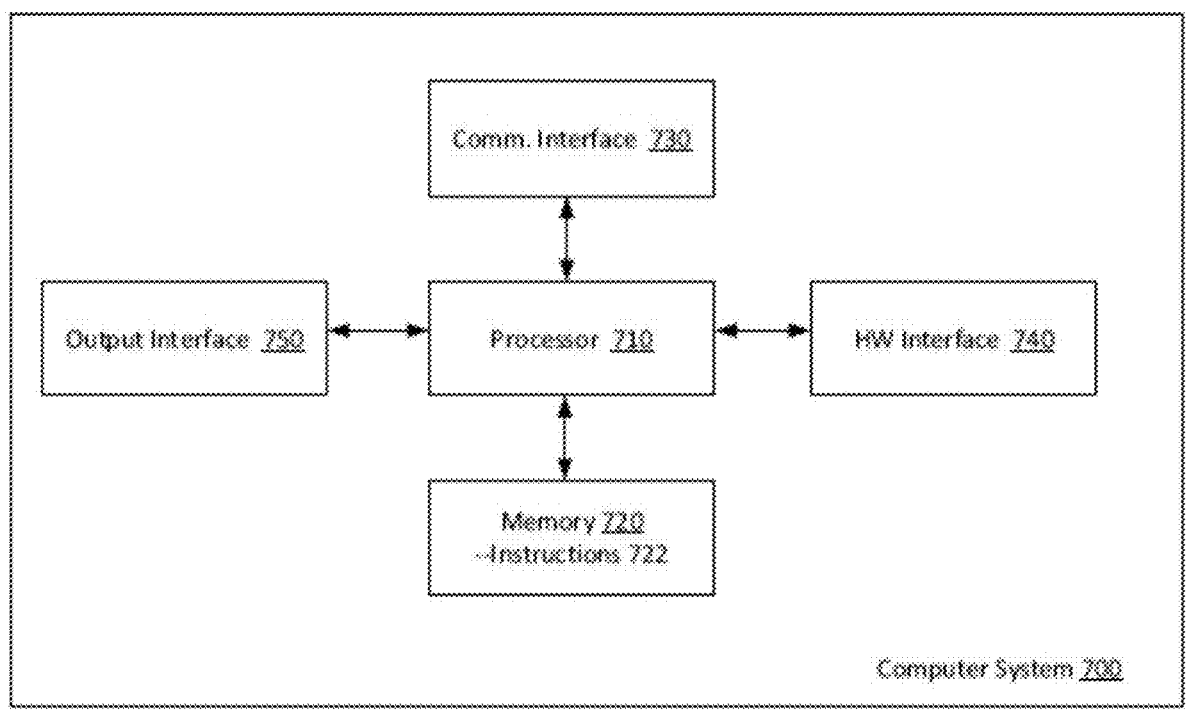
FIG. 7 schematically illustrates one example of a system as described herein.

FIG. 7 illustrates a computer system on which graft compute system 100 can be implemented, according to one or more examples. In some examples, computer system 700 can correspond to a laptop or desktop computer, mobile computing device or other user-operated computer that is co-located in a facility where an SCR procedure is performed. In other examples, the computer system 700 can be remote from the facility where the SCR is performed. In some variations, the computer system 700 can correspond to a server or network computing system. In additional variations, the computer system 700 can be implemented as a distributed system, utilizing multiple computers operating in one or more locations (e.g., at facility of procedure, remote from facility of procedure, etc.).

While numerous examples are described in which the graft compute system 100 is local to the site where an SCR procedure for implanting the graft is performed, in variations, the computer system 700 can be remote in whole or in part, to enable, for example, remote operators to determine design parameters for a graft, and/or to construct a graft in accordance with design parameters determined through the implementation of the graft compute system 100.

With further reference to FIG. 7, the computer system 700 includes one or more processors 710, one or more types of memory 720, one or more communication interfaces 730, one or more hardware interfaces 740, and one or more output interfaces 750. The processor(s) 710 can include, for example, a central processor and/or graphics processing unit (GPU). The memory 720 can store instructions 722 that are executable by the processor(s) 710 to implement the graph compute system 100. The communication interface(s) 730 can include one or more interfaces for enabling the computer system 700 to transmit and receive data over one or more communication mediums. By way of example, the communication interface(s) can include a local wireless port (e.g., Bluetooth, Wi-Fi utilizing an 802.11 communication protocols, etc.), cellular port and/or other network communication interface. The hardware interface(s) 740 can include, for example, a serial or wireless port to receive video, media or images from a connected camera. The output interface 750 can include, for example, an interface for a display or printer device.

According to examples, the processor(s) 710 can execute the instructions 722 in memory 720 to receive video data from an attached camera device using hardware interface 740. The processor(s) can further execute the instructions 722 to generate images or other output which reflect the design parameters and configurations for a graft that is to be used with an SCR procedure.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method for guiding a surgical procedure, the method comprising:
   receiving imaging data contained in a video stream captured by an in-situ imaging device that traverses a treatment site of a patient;
   processing image data from the in-situ imaging device;
   analyzing the image data to (i) detect image data that depicts a set of structures in the treatment site, (ii) determine an orientation attribute of each structure of the set with respect to a reference; and (iii) determine a respective scale factor for one or more portions of image data that depict each structure of the set, the respective scale factor of each portion of the image data reflecting a distortion in size of that portion of the image data with respect to a reference scale;
   determining geometric information for at least a portion of the treatment site where the set of structures are located; and
   calculating at least a first measurement that represents a physical span between a pair of structures of the set, based at least in part on the orientation attribute of each structure of the set, the respective scale factor of each portion of the image data, and the determined geometric information.

2. The method of claim 1, further comprising calculating at second measurement that represents a physical span between a second pair of structures of the set.

3. The method of claim 2, wherein the first and second measurements are used to determine at least one of location or dimensional information of a graft placed in the treatment site.

4. The method of claim 3, wherein the location information is a position of the graft at the treatment site.

5. The method of claim 4, wherein the position of the graft is with respect to a location of at least one of structures.

6. The method of claim 3, wherein the dimensional information is at least one of a size, width or area of the graft.

7. The method of claim 1, further comprising:
   analyzing the image data to determine anatomical characteristics of the treatment site; and
   determining the reference for the orientation attribute of the set of structures based at least in part on the determined anatomical characteristics.

8. The method of claim 1, wherein the patient has a torn rotator cuff and the surgical reconstruction is reconstruction of the patient's superior capsule.

9. The method of claim 1, processing the image data includes processing multiple frames of the video stream; and analyzing the image data includes identifying one or more markers for a target site in a first frame of the video feed, and tracking the one or more markers to one or more subsequent frames of the video feed.

10. The method of claim 9, wherein the one or more markers correspond to locations for the structures.

11. The method of claim 1, wherein the imaging device is an arthroscope.

12. The method of claim 1, wherein the image data is processed using at least one trained computer algorithm.

13. The method of claim 12, wherein processing comprises identifying one or more elements in the image data, wherein said one or more elements comprise one or more of an anatomical structure, a surgical tool, or a pathology.

14. The method of claim 13, wherein processing further comprises:
   receiving an indication from an operator to select one or more of a plurality of points or an area in said video stream;
   calculating one or more measurements for said pularity of points or selected area in said video stream; wherein said one or more measurements comprise one or more of a length, a surface area, a circumference, or a volume; and display said measurements on a displaying device intraoperatively to be used by an operator during said surgical procedure.

15. The method of claim 12, wherein the least one trained computer algorithm comprises one or more trained machine learning algorithms, one or more trained deep learning algorithms, or a combination of both.

16. The method of claim 12, wherein the image data is processed using one or more processing modules.

17. The method of claim 16, the one or more processing modules comprise at least one of a video stream decomposition module, a tool recognition module, a tool tip reference sizing module, an anatomy recognition module, a tool tracking module, a landmark establishment module, a distance aggregator module, a video blend module, a pathology detection module, a pathology sizing module, or a radiology imaging module.

18. A non-transitory computer-readable medium including contents that are configured to cause one or more processors to perform a method comprising:

receiving imaging data contained in a video stream captured by an in-situ imaging device that traverses a treatment site of a patient;

processing image data from the in-situ imaging device;

analyzing the image data to (i) detect image data that depicts a set of structures in the treatment site, (ii) determine an orientation attribute of each structure of the set with respect to a reference; and (iii) determine a respective scale factor for one or more portions of image data that depict each structure of the set, the respective scale factor of each portion of the image data reflecting a distortion in size of that portion of the image data with respect to a reference scale;

determining geometric information for at least a portion of the treatment site where the set of structures are located; and calculating at least a first measurement that represents a physical span between a pair of structures of the set, based at least in part on the orientation attribute of each structure of the set, the respective scale factor of each portion of the image data, and the determined geometric information.

* * * * *